(12) United States Patent
Wiles et al.

(10) Patent No.: US 11,110,416 B2
(45) Date of Patent: Sep. 7, 2021

(54) DEVICE AND APPARATUS FOR COLLECTING MICROBIAL GROWTH FROM A SEMI-SOLID SURFACE

(71) Applicant: BECTON DICKINSON AND COMPANY, Franklin Lakes, NJ (US)

(72) Inventors: Timothy Mark Wiles, Manchester, MD (US); Dwight Livingston, Fallston, MD (US); Jennifer Singelyn, Morristown, NJ (US); William Alan Fox, Lake Wylie, SC (US); Brian Reuben Langhoff, Julian, NC (US); Vikram Patel, Fair Lawn, NJ (US); Sean Tucker, Durham, NC (US); Ming-hsiung Yeh, New Freedom, PA (US); Michael A. Brasch, Gaithersburg, MD (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 339 days.

(21) Appl. No.: 15/564,364

(22) PCT Filed: Apr. 8, 2016

(86) PCT No.: PCT/US2016/026625
§ 371 (c)(1),
(2) Date: Oct. 4, 2017

(87) PCT Pub. No.: WO2016/164712
PCT Pub. Date: Oct. 13, 2016

(65) Prior Publication Data
US 2018/0126343 A1    May 10, 2018

Related U.S. Application Data

(60) Provisional application No. 62/144,574, filed on Apr. 8, 2015.

(51) Int. Cl.
*B01F 13/08* (2006.01)
*B01L 3/00* (2006.01)
(Continued)

(52) U.S. Cl.
CPC .......... *B01F 13/0827* (2013.01); *B01L 3/502* (2013.01); *B01L 3/5029* (2013.01);
(Continued)

(58) Field of Classification Search
CPC .... B01F 13/0827; B01L 3/5029; B01L 3/502; B01L 3/5088; B01L 2300/161;
(Continued)

(56) References Cited

U.S. PATENT DOCUMENTS

| 4,956,297 A | 9/1990 | Hood et al. |
| 7,544,961 B2 | 6/2009 | Feldsine et al. |

(Continued)

FOREIGN PATENT DOCUMENTS

| CN | 101238206 A | 8/2008 |
| CN | 101983036 A | 3/2011 |

(Continued)

OTHER PUBLICATIONS

International Search Report from PCT Application No. PCT/US2016/026625 dated Aug. 31, 2016.
(Continued)

*Primary Examiner* — Dennis White
(74) *Attorney, Agent, or Firm* — Botos Churchill IP Law LLP

(57) ABSTRACT

A device for collecting a biological sample from a semi-solid surface. The device has a shaft with a proximate end and a distal end and a tip integrated with the shaft at the proximate end. The tip has a surface adapted to collect microorganisms thereon or release microorganism from, or both, wherein the adapted surface comprises at least one
(Continued)

feature of a recess or extension to increase surface area of the tip and collect microorganisms thereon. Examples of such features include microfeatures with dimensions of about 1000 μm or less. Other examples include a pipette tip.

6 Claims, 16 Drawing Sheets

(51) Int. Cl.
*G01N 23/225* (2018.01)
*G01N 1/02* (2006.01)
*G01N 35/10* (2006.01)
*B01L 3/02* (2006.01)
*A61B 10/02* (2006.01)

(52) U.S. Cl.
CPC .......... *B01L 3/5088* (2013.01); *G01N 23/225* (2013.01); *A61B 2010/0216* (2013.01); *B01L 3/021* (2013.01); *B01L 2200/0684* (2013.01); *B01L 2300/089* (2013.01); *B01L 2300/0829* (2013.01); *B01L 2300/0896* (2013.01); *B01L 2300/161* (2013.01); *B01L 2400/043* (2013.01); *G01N 2001/028* (2013.01); *G01N 2035/106* (2013.01)

(58) Field of Classification Search
CPC ............... B01L 3/021; B01L 2400/043; B01L 2300/0896; B01L 2300/089; B01L 2300/0829; B01L 2200/0684; G01N 23/225; G01N 2035/106; G01N 2001/028; A61B 2010/0216; C12M 33/04; C12M 33/00
See application file for complete search history.

(56) References Cited

U.S. PATENT DOCUMENTS

| | | | |
|---|---|---|---|
| 8,390,924 B2 | 3/2013 | Akiyama et al. | |
| 8,921,317 B1* | 12/2014 | Burton | A61K 38/363 435/13 |
| 2002/0004020 A1 | 1/2002 | Scatizzi | |
| 2003/0179916 A1* | 9/2003 | Magnuson | G01N 33/5005 382/128 |
| 2005/0226785 A1 | 10/2005 | Colville | |
| 2007/0081419 A1 | 4/2007 | Mou | |
| 2007/0249961 A1 | 10/2007 | Morrison et al. | |
| 2008/0131326 A1 | 6/2008 | Pelletier et al. | |
| 2008/0272283 A1* | 11/2008 | Feldsine | G01N 21/76 250/229 |
| 2009/0054809 A1 | 2/2009 | Morishita et al. | |
| 2011/0146419 A1 | 6/2011 | Gonzalez et al. | |
| 2011/0146420 A1 | 6/2011 | Okada et al. | |
| 2011/0167934 A1 | 7/2011 | Sales | |
| 2012/0021940 A1* | 1/2012 | Guthold | C12N 15/1068 506/9 |
| 2014/0242570 A1* | 8/2014 | Botma | C12M 33/00 435/3 |

FOREIGN PATENT DOCUMENTS

| | | |
|---|---|---|
| CN | 102203579 A | 9/2011 |
| CN | 101990631 B | 8/2014 |
| EP | 0357892 A1 | 3/1990 |
| EP | 2333511 A1 | 6/2011 |
| GB | 2173304 A | 10/1986 |
| GB | 2500658 A | 10/2013 |
| JP | S61-228351 A | 10/1986 |
| JP | H02-074243 A | 3/1990 |
| JP | H02-245174 A | 9/1990 |
| JP | H05-64737 B2 | 9/1993 |
| JP | H08-154660 A | 6/1996 |
| JP | 2006502376 A | 1/2006 |
| JP | 2007531894 A | 11/2007 |
| JP | 2012120487 A | 6/2012 |
| WO | 2007016618 A1 | 2/2007 |
| WO | 2009102835 A1 | 8/2009 |
| WO | 2010024042 A1 | 3/2010 |

OTHER PUBLICATIONS

Japanese Office Action issued in JP application No. 2017-553179 dated Feb. 4, 2020, pp. 15.
Brazilian Office Action issued in corresponding BR Application No. BR112017021460-1 dated Jul. 17, 2020 (7 pages).
Chinese Office Action issued in corresponding CN application No. 201680033172.6 dated Jul. 9, 2020.
European Office Action issued in corresponding EP application No. 16 777 347.2 dated Jun. 23, 2020.
European Office Action issued in corresponding EP Application No. 16777347.2 dated Jan. 29, 2021, pp. 5.
Japanese Office Action issued in JP application No. 2017-553179 dated Jan. 5, 2021, pp. 8.
Notification of Second Office Action in corresponding Chinese Patent Application No. 201680033172.6 dated Apr. 15, 2021,16 pp.
Office Action issued in corresponding Brazilian Application No. 112017021460-1 dated Feb. 9, 2021, 14 pp.
Second Examination Report issued in corresponding Australian Patent Application No. 2016245891 dated Apr. 30, 2021, 3 pp.
European Search Report dated Oct. 17, 2018 received in EP16777347, pp. 12.
First Examination Report issued in IN patent application No. 201717037545 dated Jun. 8, 2021, 7 pp.

* cited by examiner

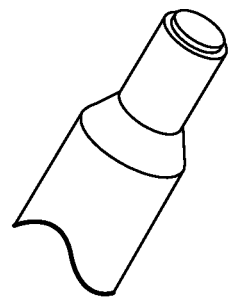
FIG. 2D
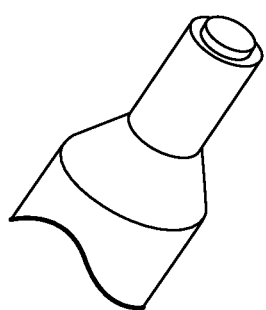
FIG. 2C
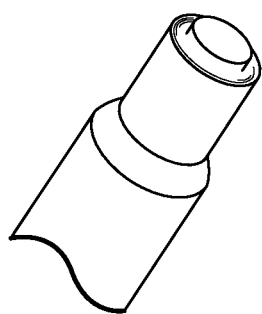
FIG. 2F
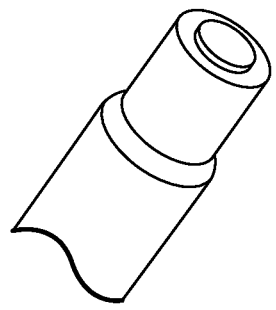
FIG. 2B
FIG. 2E
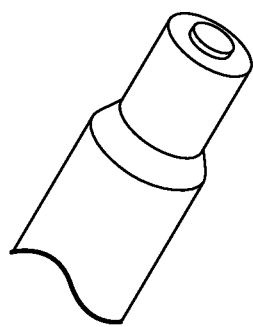
FIG. 2A

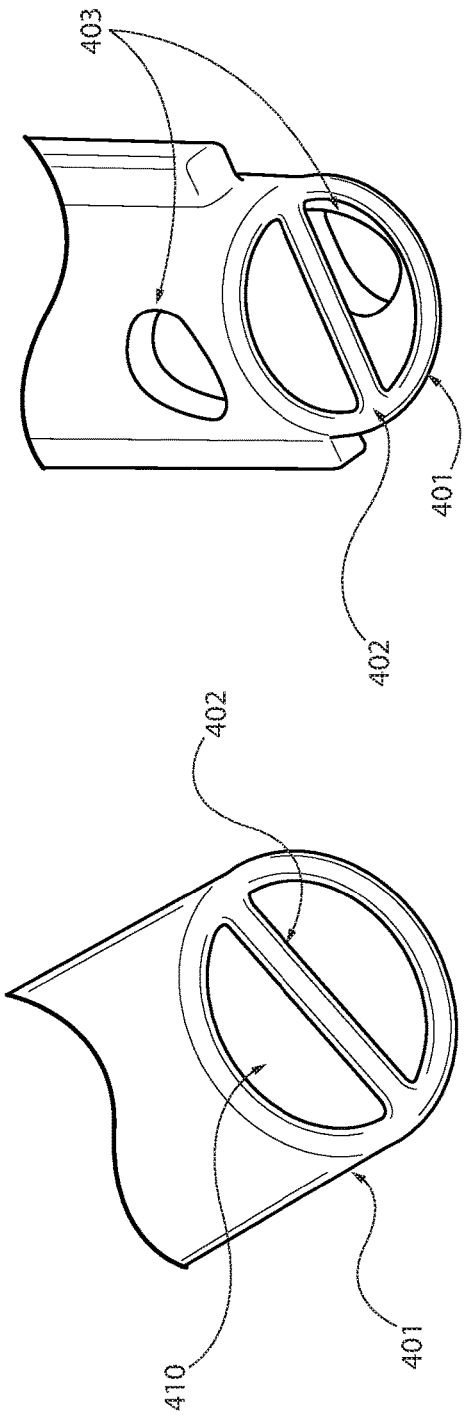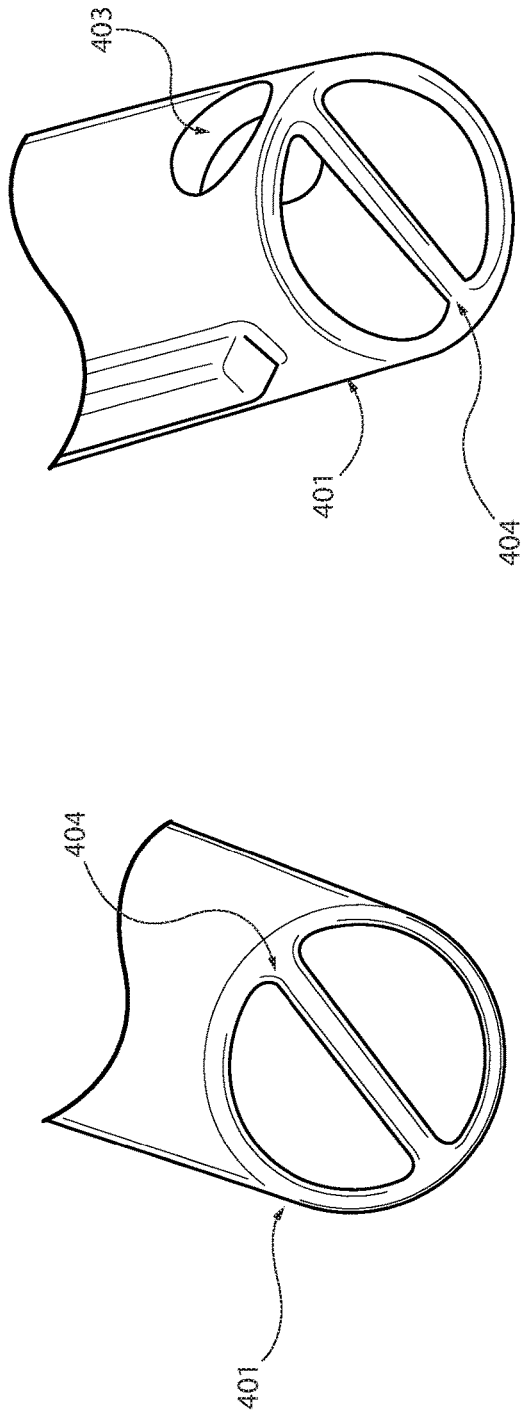

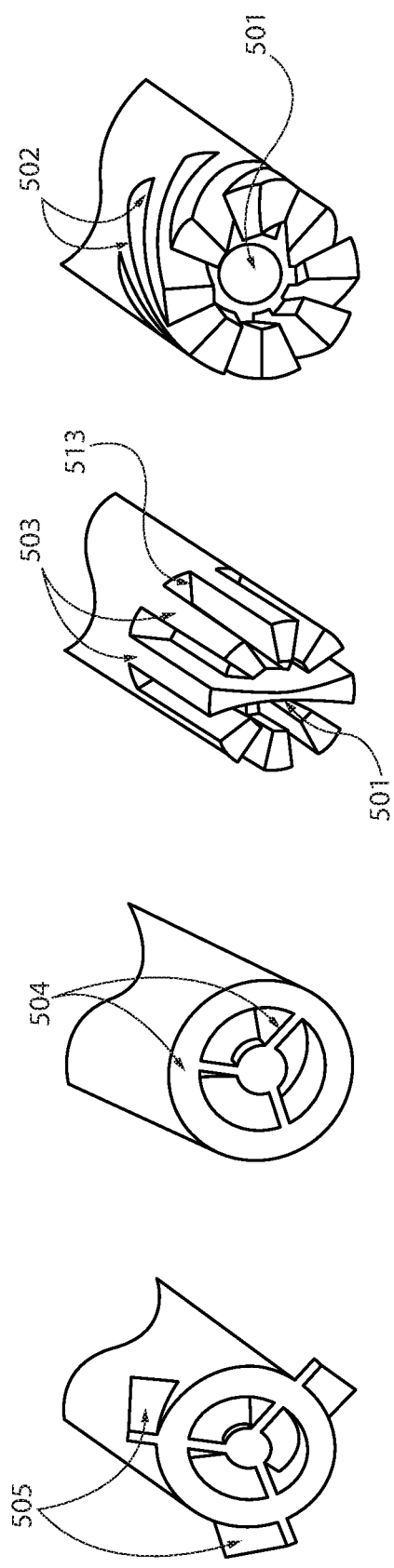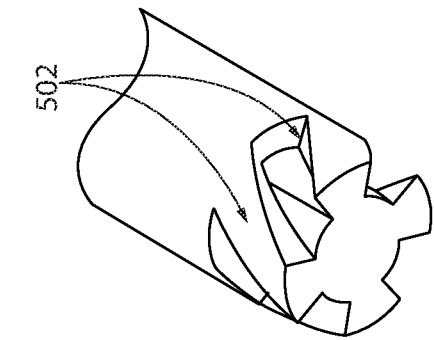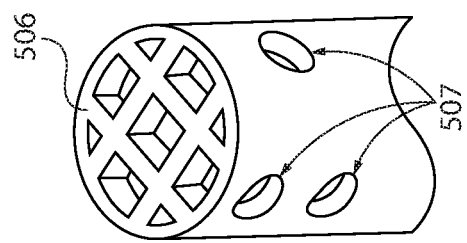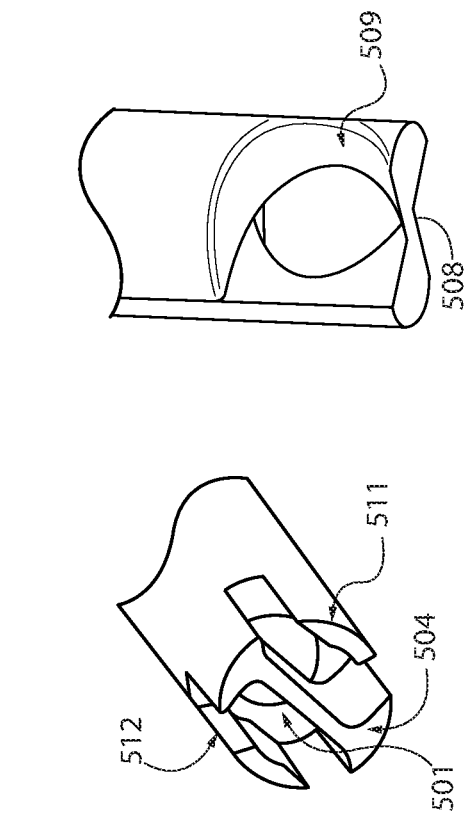

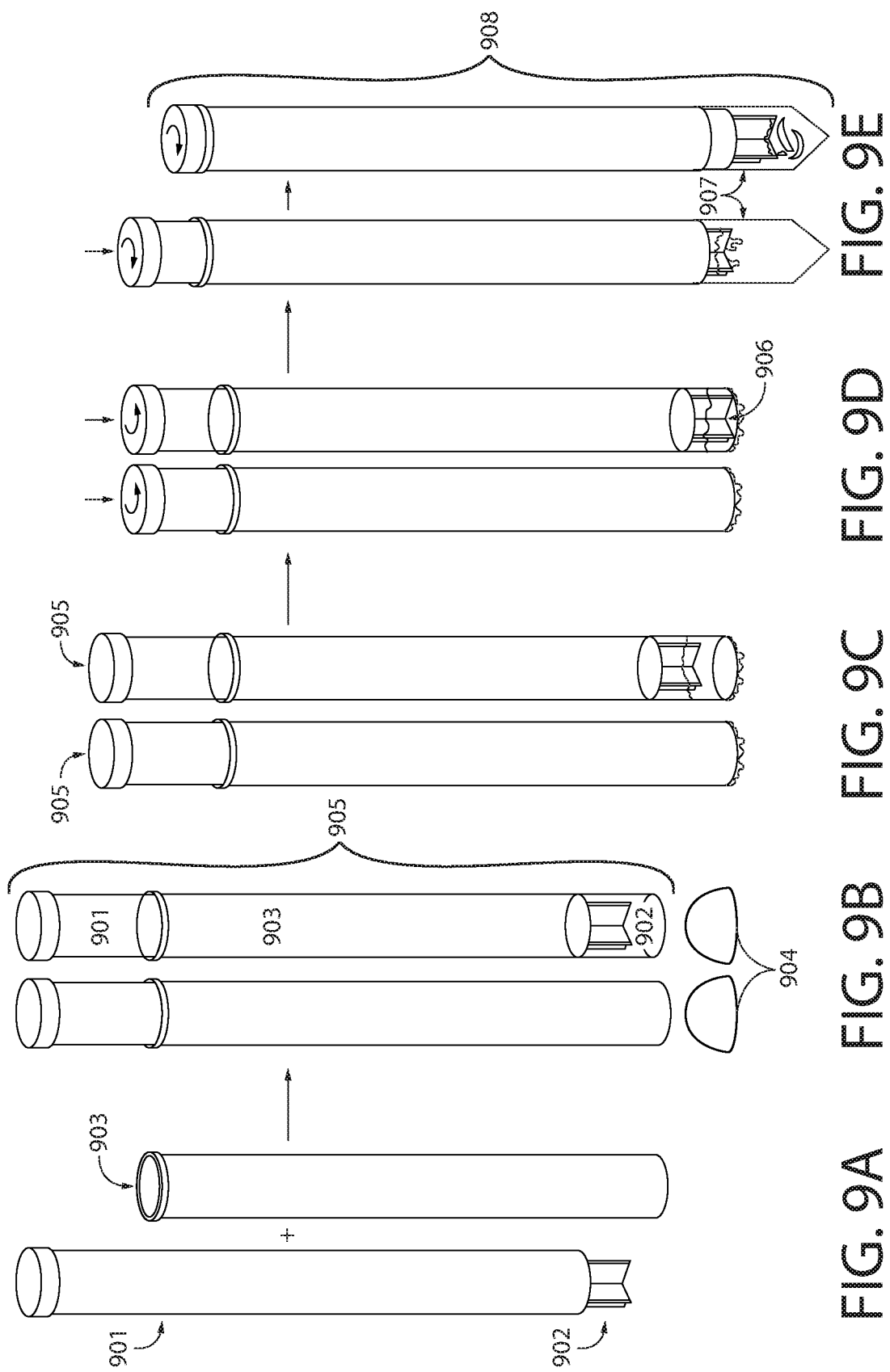

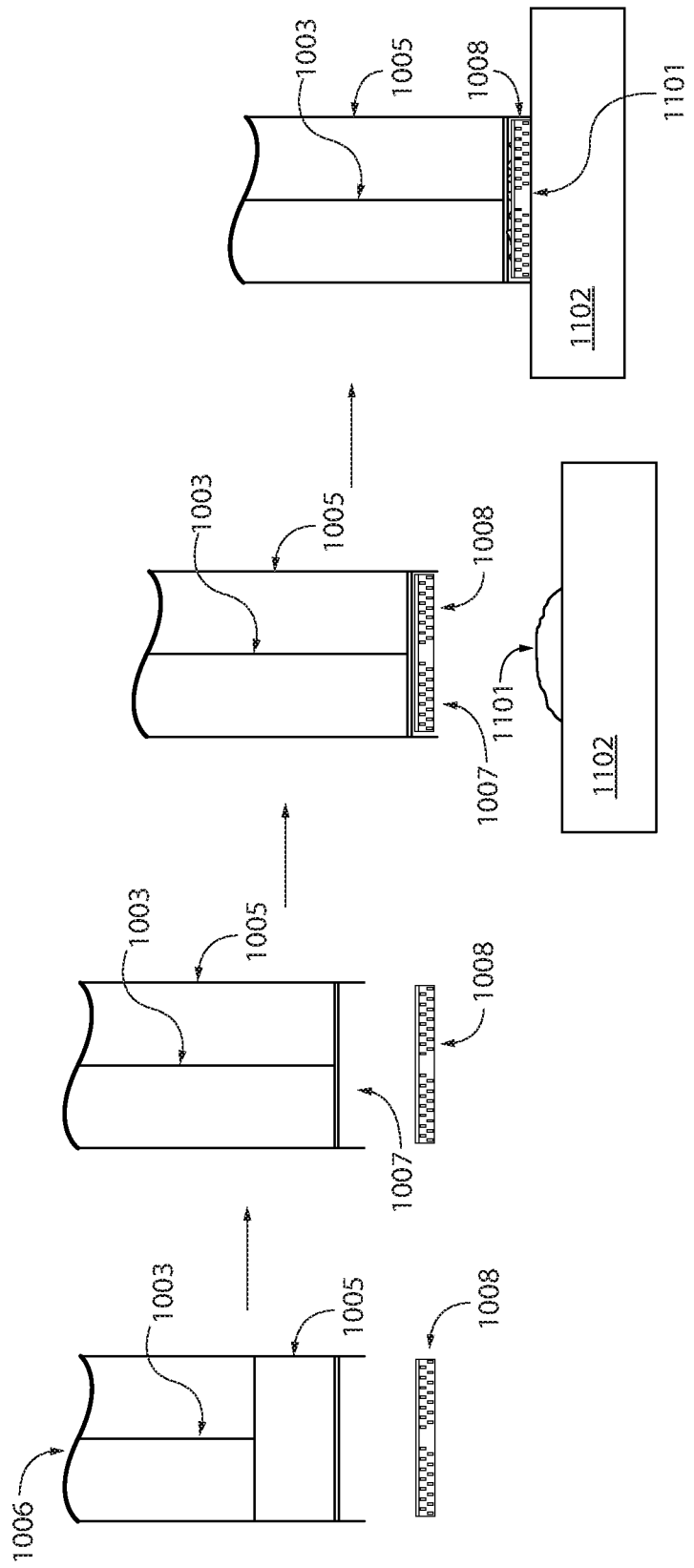

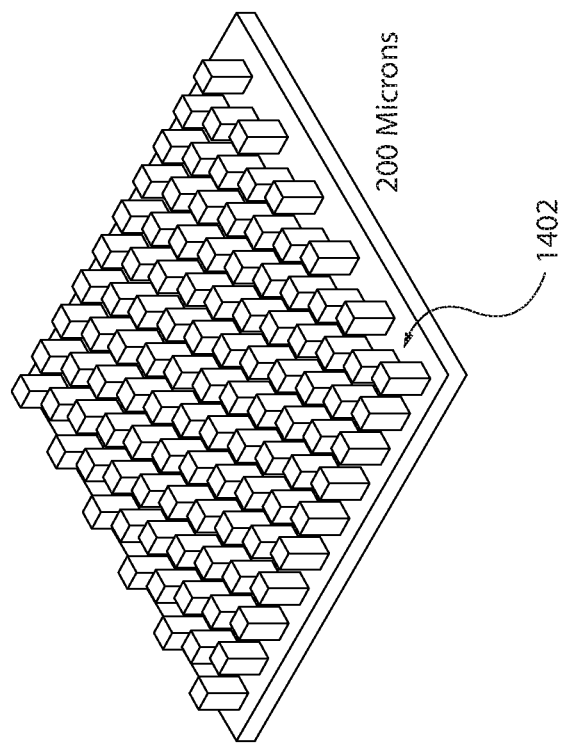
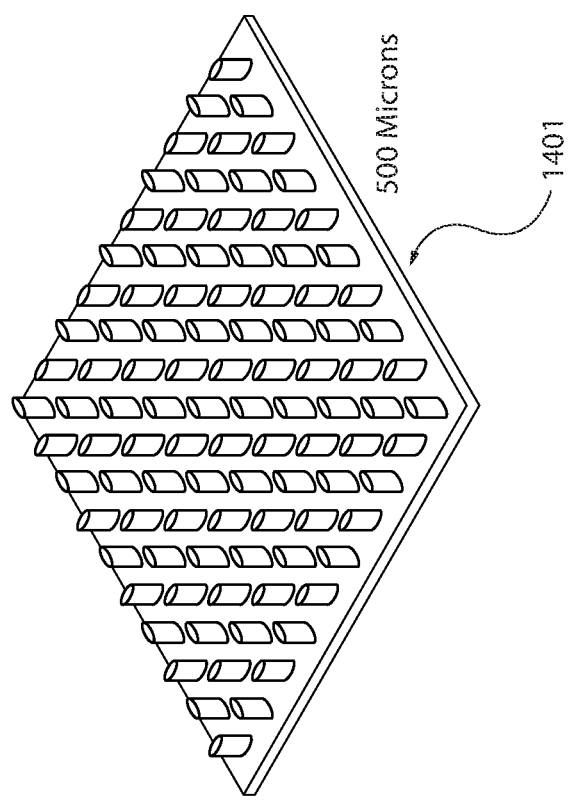
FIG. 15

DEVICE AND APPARATUS FOR COLLECTING MICROBIAL GROWTH FROM A SEMI-SOLID SURFACE

CROSS-REFERENCE TO RELATED APPLICATION

The present application is a national phase entry under 35 U.S.C. § 371 of International Application No. PCT/US2016/026625 filed Apr. 8, 2016 published in English, which claims priority from U.S. Provisional Application No. 62/144,574, filed Apr. 8, 2015, all of which are incorporated herein by reference.

BACKGROUND OF THE INVENTION

Disclosed herein is a device and apparatus for collecting one or more samples containing microorganisms from colonies of microorganisms grown on a semi-solid surface for preparation of a suspension of microorganisms in a liquid solution.

As a routine practice in medical diagnosis, biological samples such as blood are extracted from patients and analyzed to diagnose and treat illnesses. Depending upon indications, the samples may be analyzed to determine if microorganisms are present in the sample, e.g., by blood culture (such as the BACTEC™ FX and BACTEC™ 9000 series from Becton, Dickinson and Company) or by streaking onto an agar plate (manually or by an automated instrument such as the Innova™ sold by Becton, Dickinson and Company). If microorganisms are determined to be present, there is both medical and economic justification to both identify the specific microorganism present and, to facilitate treatment, the antibiotic resistance/susceptibility of the microorganism.

Many kinds of microorganism (which will also be referred to below as microbes), particularly bacteria and unicellular fungi, can be identified by mass spectrometric ("mass spec") processes, such as Matrix Assisted Laser Desorption Ionization ("Maldi"). It is also desirable to analyze the effectiveness of an antimicrobial agent in inhibiting the growth of microbial isolates from clinical specimens. Such analysis is known as antimicrobial susceptibility testing ("AST"). In preparation for both MALDI and AST analyses, microbial colonies are collected from a semi-solid media to be used in making a heavy suspension sample.

Commonly, the process of picking sample from colonies for sample preparation is a manual process. Although there have been advancements toward automated systems, the current automated processes and devices remove only a small amount of sample from a single colony. These devices require numerous picks in order to remove the biomass contained in several colonies to acquire enough sample necessary for downstream testing (e.g., MALDI or AST). Additionally, these systems use a direct smear process of applying microbes directly to the Maldi preparation plate. Improved devices for efficiently collecting microbial growth for use in a suspension sample are sought.

BRIEF SUMMARY OF THE INVENTION

The device disclosed herein is a "one pick tool" for collecting microorganisms grown on a semisolid surface for preparation of a suspension of microorganisms in a liquid solution that can be used for further identification (using MALDI or other technique) and/or AST testing.

One embodiment of the present invention comprises a shaft and tip assembly. The shaft has a proximate end and a distal end wherein a tip is affixed to and extends from the shaft. The tip has an adapted surface where microorganism is collected when the tip is brought into contact with a colony of microorganisms. The adapted surface may be a grid pattern or vary in diameter. The adapted surface may also comprise of blades, knobs, spikes or ridges. The adapted surface can also assist in the release of the microorganism.

In another embodiment, the assembly has a cavity and a vented channel or multiple vented channels located on or near the proximate end of the shaft thereby providing an adapted surface for the collection of microorganisms. The cavity may be covered by a grid or may contain one or more blades. The blades may be helical or straight or may extend from the cavity.

In yet another embodiment, the assembly may have a removable tip. The removable tip may be a sheath attached to the proximate end of the assembly by magnetic force, compression or screw threading. The sheath may contain a scoop to further facilitate microorganism collection.

In another embodiment, the pick tool may have a rod and blade assembly that extends through a sleeve. The rod has a proximate end and a distal end, wherein the distal end is a neutral extension to facilitate handling of the tool. The proximate end of the rod has a blade or blades extending radially. Once the pick tool has located and confined a selected microorganism sample, the rod and blade assembly are capable of being advanced down the sleeve by manipulating the distal end of the rod to facilitate collection of microorganism. The rod and blade assembly are also capable of being retracted by manipulation of the distal end to facilitate release of the microorganism.

In yet another embodiment, the pick tool has a non-magnetic rod and magnetic bar assembly. The non-magnetic rod has a distal end and a proximate end where the distal end is a neutral extension to facilitate handling of the tool. The magnetic bar extends radially from the proximate end of the non-magnetic rod. The assembly is housed in a tube with at least a top opening that permits free rotation of the magnetic bar. The tube has a bottom portion that extends beyond the assembly forming a recess. This embodiment further comprises a ferromagnetic wire attached to the top of a scraper creating the scraper assembly. The scraper assembly is magnetically attached to the magnetic bar in the recess of the tube. Once the pick tool has located a selected microorganism, the distal end of the non-magnetic rod is manipulated to collect microorganism in the recess of the tube with the scraper assembly. The distal end of the non-magnetic rod can also be manipulated to facilitate the release of microorganism from the recess of the tube. The distal end may be manipulated manually or automatically. Some aspects of the The present invention is described in further detail below.

BRIEF DESCRIPTION OF THE DRAWINGS

FIG. 2A-F illustrate detail views of embodiments of the tips of end portions in FIG. 1.

FIG. 4A-D illustrate detail views of alternative tip geometries for the end portion of the pick tools illustrated in FIG. 1.

FIG. 5A-I illustrate detailed views of additional features of tip geometries for the end portion of the pick tools illustrated in FIG. 1.

FIG. 9A-E are perspective views illustrating one embodiment of the pick tool and the one pick process for collecting and releasing sample.

FIG. 11A-D illustrates the magnetic stirrer assembly of one embodiment of the present invention.

FIG. 15 illustrates microfeature patterns that are one embodiment of the present invention.

DETAILED DESCRIPTION

Figure 1:
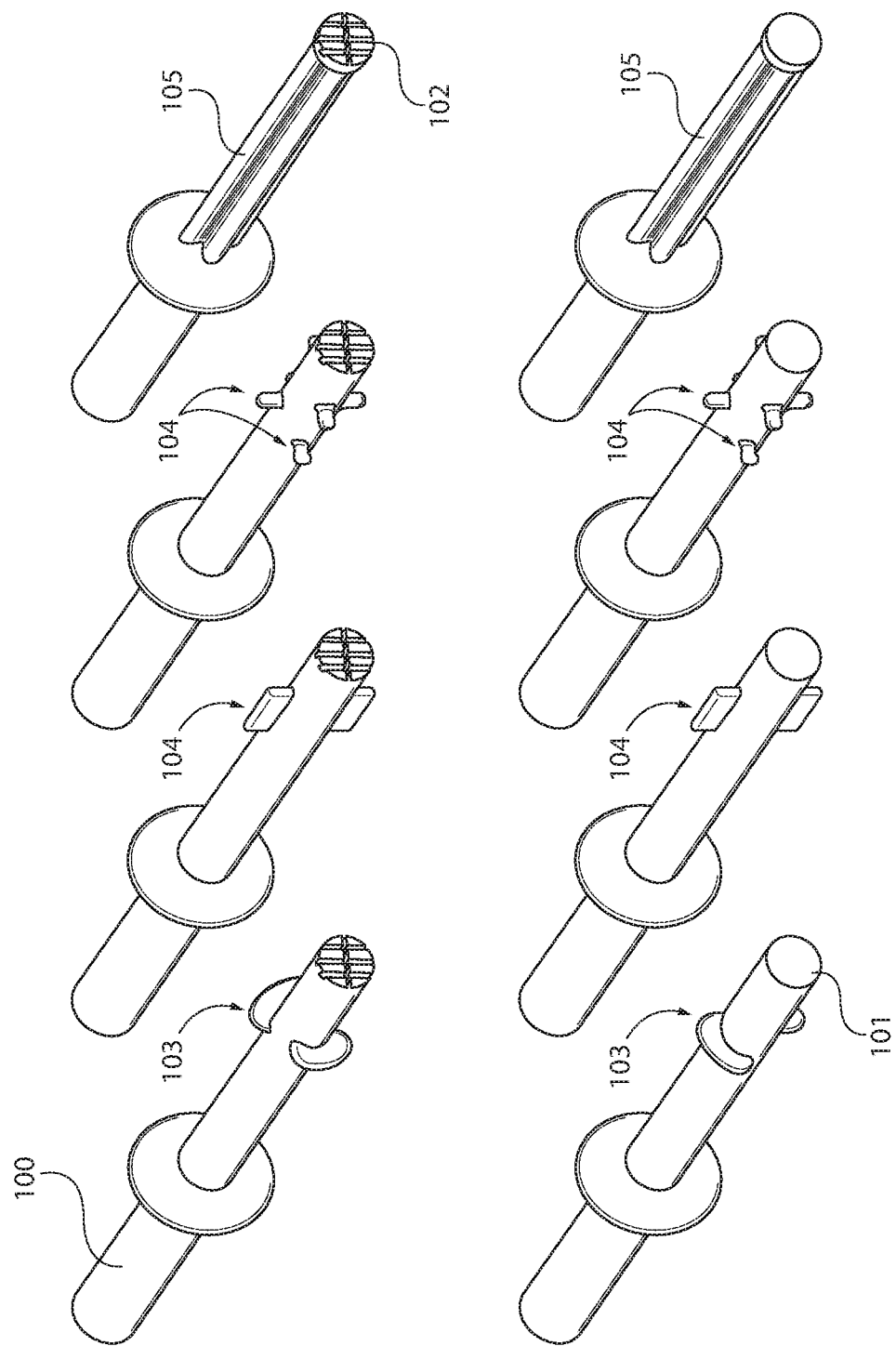
FIG. 1 illustrates embodiments of the end portion of the pick tool described herein.

The embodiments of the pick tool disclosed herein are able to pick a desirable amount of biological sample from a surface. As noted above, pick tools are used to collect sample (e.g., microbes such as bacteria, fungi, etc.) in the form of colonies formed on the surface of a nutrient media (referred to as agar, culture media, etc.). The amount of sample collected by the pick tools described herein is will preferable be sufficient to prepare a heavy suspension (about $1 \times 10^7$ to about $1 \times 10^{10}$ CFU/ml) of microorganism in liquid solution. Target is about $3 \times 10^8$ CFU/ml. In preferred embodiments, the tool is able to acquire sufficient sample in one pick. The "one pick" tool is configured to have a sample collection surface adapted to acquire in a single pick sufficient sample to prepare a heavy suspension that will be used for subsequent Maldi identification. In preferred embodiments, the same suspension will also be used as the source of the sample for antimicrobial susceptibility testing (AST).

The pick tool comprises a shaft and tip assembly. The shaft is a neutral extension that facilitates handling of the tool. The shaft has both a distal end and a proximate end. The distal end of the shaft can be automatically or manually manipulated to facilitate the pick and release processes. The proximate end of the pick tool comprises a tip with an adapted surface for the collection or removal of microorganisms. The tip may be a separate component of the shaft or the shaft and tip may be monolithically integrated.

The tool is intended to be part of an automated picking system, whereby the tool is received by a robotic device or other suitable mechanical carrier for the tools described herein. Robotic devices and other mechanical devices suitable for use in carrying and manipulating the tools described herein are well known to one skilled in the art and are not described in detail herein. The tools described herein can also be handled manually, although automated operation of the tool is preferred.

The tool can be attached to its carrier in a variety of ways. For example, the tool may be attached magnetically, using suction or by mechanical attachment (e.g., a threaded male portion received by a threaded female portion of the carrier or by frictional fit). The various ways in which the tool may be attached to the carrier are well known to one skilled in the art and are not described in detail herein. The tool may also be attached in a press fit manner so that the tool "snaps on" its carrier and is removing therefrom by being pushed off or pulled off. The tool is typically removed from the carrier once the collected sample has been released from the tool for further processing.

The pick tool is carried to the surface on which the target sample is disposed. Typically, the surface is a culture media surface on which colonies of sample have formed. In those embodiments where the pick tool is carried by a robotic device, the device senses the relative position of the pick tool and media and advances the pick tool to the location on the surface of the media where the target colony is located. After the pick tool acquires sample, the pick tool is withdrawn from the media surface thereby removing sample from the surface of the agar disposed in the culture plate (e.g., a culture dish or petri dish). The device can remove sample from multiple colonies without washing between picks provided cross-contamination between colonies is not a concern.

The pick tool may have an adapted picking surface with features or modifications (e.g., flocked, porous, rough, molded, textured, aperture or cavernous features) to facilitate pick and/or release of the sample. The overall dimensions of the picking surface with dimensions that are about 1 to about 2 millimeters. The dimensions of the picking surface are limited by the size of the pick tool and the size of the colonies to be picked. The adapted surface modifications are a matter of design choice, and the factors that influence the selection of the adapted surface are the size of the pick tool, the size of the colonies and the texture and other properties of the colonies. In certain embodiments these surface adaptations or modifications may be considered microfeatures as they have a feature size of about 1000 μm or less. In certain embodiments the microfeatures have one or more dimensions on the order of about 100 μm to about 500 μm. Microfeatures, as used herein, in include features with dimensions on the nanometer scale up to about 1000 μm. The microfeatures can be oriented in a wide variety of regular patterns and irregular arrangements. Many examples are provided herein for purposes of illustration. The adapted surface of the tool also may have features, such as vents or capillary type gaps, which allow the microorganisms to be received into cavities in the tools when colonies are picked. These or other features (e.g., vents, holes, etc.) may also facilitate microorganism removal from the tool by allowing liquid to flow through the tool as the pick tool is placed in solution for release of microorganisms into the solution.

The pick tool may be rotated, moved vertically up or down or otherwise manipulated to acquire the biomass from the semi-solid media surface. Upon placement into solution, the tool may be agitated to facilitate release. For instance, the tool may be rotated, vibrated or moved up and down to effect release of sample from the tool and into solution for further processing. The tool may also incorporate or be associated with a stirring mechanism that will further facilitate release of the sample from the pick tool or the subsequent homogenization of the picked sample in the suspension.

A variety of embodiments of the one pick tools are described in the figures below.

FIG. 1 is a perspective view of a number of embodiments of the invention described herein. FIG. 1 illustrates the end portion of the pick tool (i.e., shaft 100 and top). The shaft 100 is received by or otherwise attached to the handle of the pick tool. The pick tools herein can be used manually or in an automated system. In a manual system, the pick tool shaft has a handle on the distal portion of the tool for manual manipulation of the tool. In an automated system the pick tool shaft 100 is received by a robotic mechanism. As stated above, the pick tool is attached to the robotic mechanism by any conventional attachment mechanism (e.g., press fit, suction, threaded coupling, etc.), and the robot is manipulated to position the pick tool to collect the sample and deposit the sample for further processing. The tip on the proximate end of the shaft 100 has a surface that is adapted to collect sample. The tip may have a flat surface 101 or contain features such as a grill or grid surface 102 that facilitate capture of the biomass by simple contact of the tip to the colony to be captured. The tip may also have curved blades 103, straight blades 104, small knobs 105, ridges 106 or other configurations to facilitate release of the sample from the tip and into solution.

FIG. 2 illustrates various embodiments of the tool. FIG. 2A-2D show variations in the diameter of the pick tool. The tool may be of a very small diameter (0.5 mm) to pick up very small colonies that are not well separated. Alternately, the tool can be of a larger diameter (10 mm) to pick up a large colony. FIGS. 2E and 2F show various different surface variations for the pick tool. The skilled person is aware of the precision required for colony pick and the need to avoid picks from one or more adjacent colonies. Furthermore, agar surfaces can vary (e.g., chocolate agar has a different surface and consistency than Sabouraud's dextrose agar). The accuracy of microorganism collection from different agar surfaces is affected by the pressure of the pick tool on the agar (a smaller pick tool surface area will exert more force on the agar). The weight of the tool can also affect the accuracy of the colony pick with heavier tools digging further into the agar than lighter ones. Assuming the weight of the tool stays constant, a tip with a larger surface area may be used with softer agar surfaces while a tip with a smaller surface area may be used on harder agar surfaces to increase the pressure of the pick tool on the agar during the pick.

Figure 16:
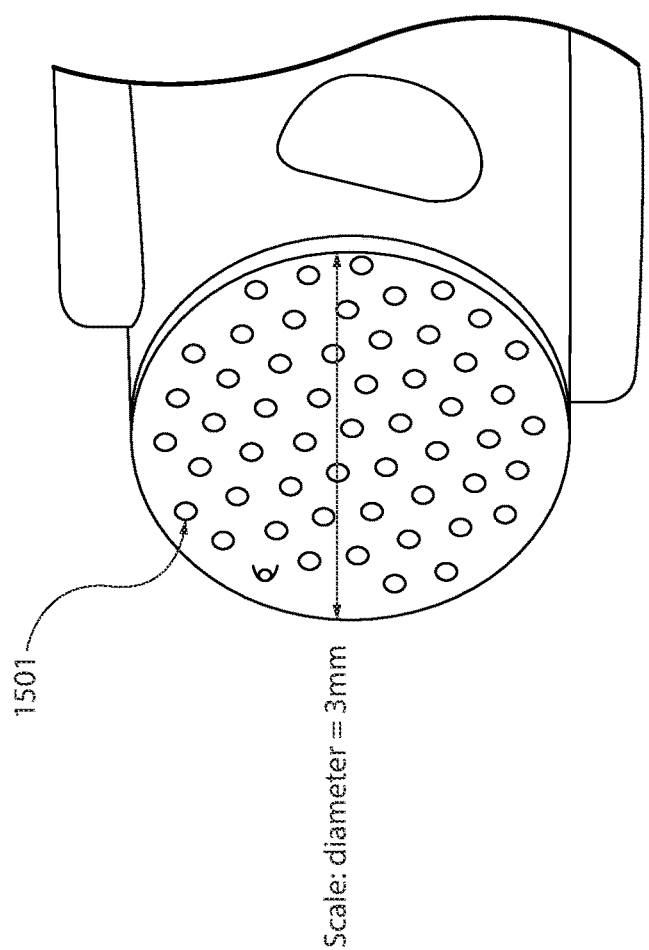
FIG. 16 illustrates pick tools having the microfeature patterns of FIG. 15.

In certain embodiments, the pick tools have micro or nano patterns, features or surface modifications, which are referred to herein as microfeatures. Microfeatures have dimensions of about 1000 µm or less. In some embodiments, the microfeature size is in the range of about 100 µm to about 500 µm. Referring to FIG. 15, there are two examples of microfeature patterns illustrated. Such features are illustrated as 1401, 1402. These features provide surfaces that control surface tension, friction, etc. Such are provided in a variety of materials. The illustrated patterns can be formed using conventional processes for providing such patterns. For example, such patterns can be molded elastomeric material, stamped, etched, etc. Such patterns can serve as microfeatures on pick tool tips, like those tips illustrated in FIGS. 2A-2F or elsewhere herein. Such patterns are illustrated on the tips of pick tools in FIG. 16 that have a diameter of about 30 mm. The microfeatures 1501 illustrated in FIG. 16 are about 100 µm to about 500 µm in dimension.

Figure 3C:
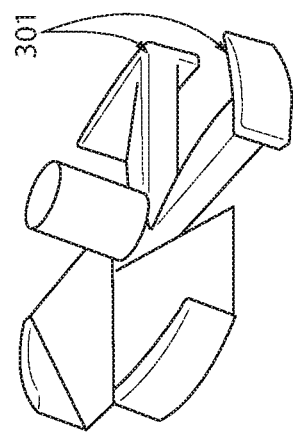
FIG. 3A-C illustrate detail views of alternative tip geometries for the end portion of the pick tools illustrated in FIG. 1.
Figure 3B:
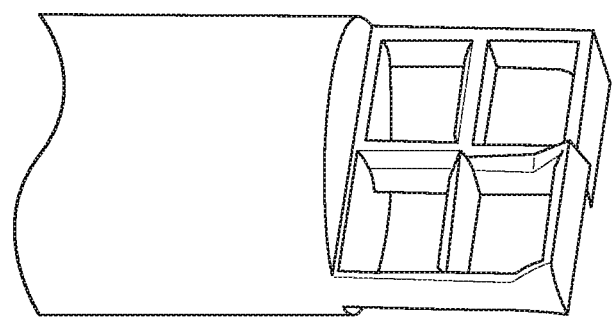
Figure 3A:
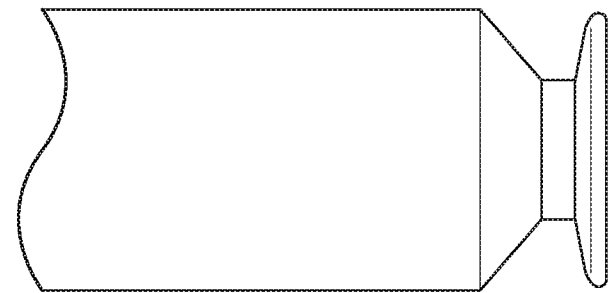

FIG. 3 depicts adapted tip geometries that include space above the contact surface for sample collection. The tip may be a flat surface with a recessed portion as illustrated in FIG. 3A, where the sampled biomass will be retained during collection. In another embodiment, the tip has an apertured capture surface illustrated as a scaffold in FIG. 3B. In other embodiments, the tip has lipped extensions 301 from the shaft as illustrated in FIG. 3C. The lipped extensions 301 are sloped to cause sample biomass to advance onto and up the slope of the extension as the shaft turns. The slope has a raised extension edge to keep the sample on the extension as it advances up the slope. The lipped extensions 301 also aid in release of the biomass sample because shear force generated by moving the pick tool in solution causes the solution to force the sample off of the tool.

FIG. 4 further illustrates other embodiments of tips able to capture sample biomass. The tips may have a collar 401 around the perimeter and a bisecting bar or scraper 402, 404 through the center of the tip. The collar 401 aids in sample biomass collection by providing a reservoir to hold the biomass, while the bisecting scraper 402, 404 shovels the biomass into the collar reservoir as its being rotated. FIGS. 4A and 4B show a straight bisecting scraper 402 while FIGS. 4C and 4D illustrate a helical bisecting scraper 404.

The tip may also have one or more vented channels 403 extending through the tip. The vented channels facilitate sample biomass collection by forcing the biomass sample into the tip interstices as the tip is rotated in contact with the biomass to be sampled. The vented channels 403 also allow the sample biomass to be dispensed into solution from the tip. On release, solution into which the sample is released (e.g., broth, water, etc.) flows through the channels 403 forcing sample from the tip cavities. FIGS. 4B and 4D illustrate a pick tool embodiment having vented channels.

FIG. 5A-5I illustrates additional embodiments of the tips for pick tools according to the present invention. The tip may have a center hole 501 encircled with "blades" (as in propeller blades) that can have a variety of configurations such as tuliped 503 or paddle type 504 or propeller 505 and arranged in a variety of configurations (e.g., helical 502, straight 503 or 504). Such "blades" provide deeper recesses that facilitate better sample biomass collection and retention. The blades can extend from the tip as in 502, 503 and 505 or be embedded in the tip as in 505.

Referring to FIG. 5E a central surface feature 504 is on the tip and will bisect the colony on contact and begin pressing the material up into the recessed pockets 501. This feature also acts as a surface scraper when the tool is rotated, completing the removal of the colony material from the agar surface. In this embodiment there is a recessed pocket on either side of the central surface feature 504.

Additional scrapers 511 on the circumference of the tool illustrated in FIG. 5E hold the picked colony material within the recessed pockets 501 during rotation.

Four slide slots 512 allow flow of the diluent water to access the recessed pockets 501 on rotation when submerged in diluent during sample release from the pick tool into solution. The flow of diluent through the recesses 501 dislodge the picked colony material collected in the recesses 501.

Certain embodiments of the pick tool assemblies contemplated herein have a shoulder feature (not shown) on the central pin or tube 522 to allow the pick tool to be ejected from the Picking Module.

Referring again to FIG. 4A, another embodiment is a pick tool that has a central hole or aperture 410 but without the bisecting scraper 402. In this embodiment, if the Pick Module to which the hollow core pick tool is attached has pneumatic or fluidics capabilities, this hollow core or passage functions as a "straw feature" to help pull or draw material up and also allow diluent to flow in both directions as needed to help dislodge material. In this embodiment, the fitting for the hollow core pick tool would include an air lead, under control of the instrument, such that positive and negative air flow could be supplied through the straw. This permits: i) pulling colonies from the plate; push colonies into the diluent into which the colonies are dispensed for further analysis; iii) is an inexpensive solution; iv) avoids problems of sensitivity of colony transfer to the surface wettability of the pick tool tip; provides for adjustable pull & push pressure or volume to provide the conditions suited for different colony types (i.e., colonies of different densities and consistencies have different requirements for collection and dispense); v) collect more colonies from a smaller diameter area by "vacuuming" colonies from the surface; vi) the pick tool can be preloaded with solution to assist dispense and mixing; and permits low-aerosol mixing with the air assist for collection and dispense.

The embodiment of FIG. 5C is a referred to as a tulip design. This tip configuration will pull up and hold liquid (on the order of 25 µl in one embodiment but the amount of fluid taken up by a particular tip is largely a matter of design choice) of liquid to make serial dilutions from micro-titer wells in a micro-titer tray. The design used capillary characteristics to hold fluid within the "tulip petal" 503 slots 513 during a rotation in the target fluid and then the slots allowed the retained fluid to mix with the next dilution tube after transfer and rotation. The slots 513 induce fluid to flow between the petals 503, dislodging collected sample therefrom.

The tip in FIG. 5C can be integrated with the hollow tube discussed above to provide the combined advantages of both designs. The embodiment of FIG. 5C provides angled "petals" or "cutters" 503 that will dislodge the specimen (e.g., bacteria) collected thereon, as in embodiments illustrated in FIGS. 5D and 5H. There is a central cavity 501 as illustrated in the embodiment of FIG. 5D. The central cavity 501 holds the collected bacteria as does the embodiment illustrated in FIG. 5D.

Figure 5I:
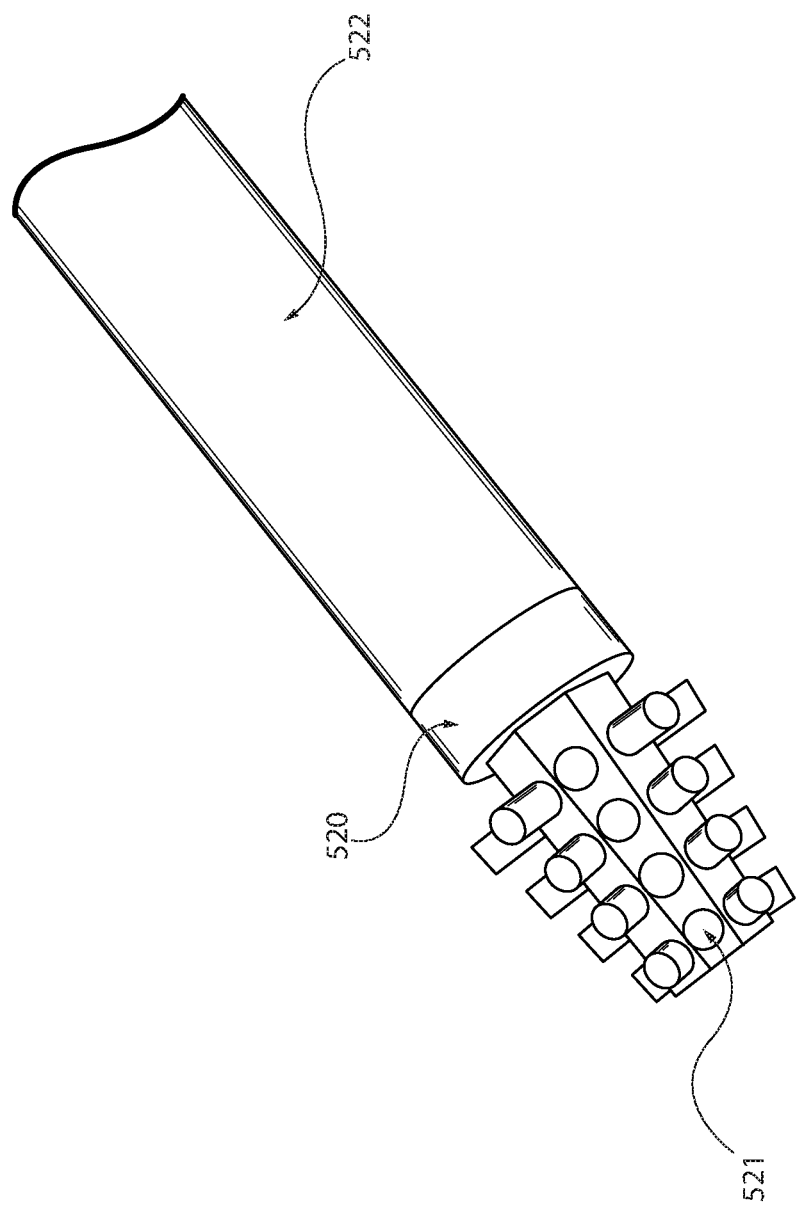

Referring to FIG. 5I, a recessed feature 520 in the top of the pick tool tip to allow the tool 521 to be picked up with a central pin or tube 522 on the Picking Module (not shown). The features 521 in the embodiment of FIG. 5I are elastomeric bristles that provide a brush like construction. In one embodiment, the elastomeric bristles can be configured as microfeatures such as those described above.

As noted above, a particular pick tool design is selected based on the characteristics of the colony that is the target of the pick. Applicants note that bacteria colonies can be hydrophilic, anionic, conductive, etc. If hydrophilic bacteria are being collected, it is advantageous if the tip is also hydrophilic. In such embodiments, the surface tension of the features (i.e., the cutters 503) retains the collected hydrophilic sample thereon.

Hydrophilic features can be provided by coating the tip with self-assembled monolayers using polycations (e.g., PDDA, PAH, etc.) or poly-anions (PSS).

Also, if the tips are anionic, they can further aid in release of the bacteria into the diluent. For such tips, an example of a material that will provide such an anionic surface is PSS (Poly(sodium 4-styrenesulfonate)) as the final self-assembled monolayer.

If the tips are conductive, this enables the position of the tip to be detected relative to the agar surface using capacitance detection.

In another embodiment, the tip surface is an open grid 506 or mesh, similar to the scaffold feature previously referenced, with side channels 507 that allow air to be easily displaced as sample is acquired. In another embodiment, the tip has a loop type projection 508 with scooping surfaces 509. In other embodiments, the tip is hollow or concave with vented channels to facilitate sample collection.

Figure 6B:
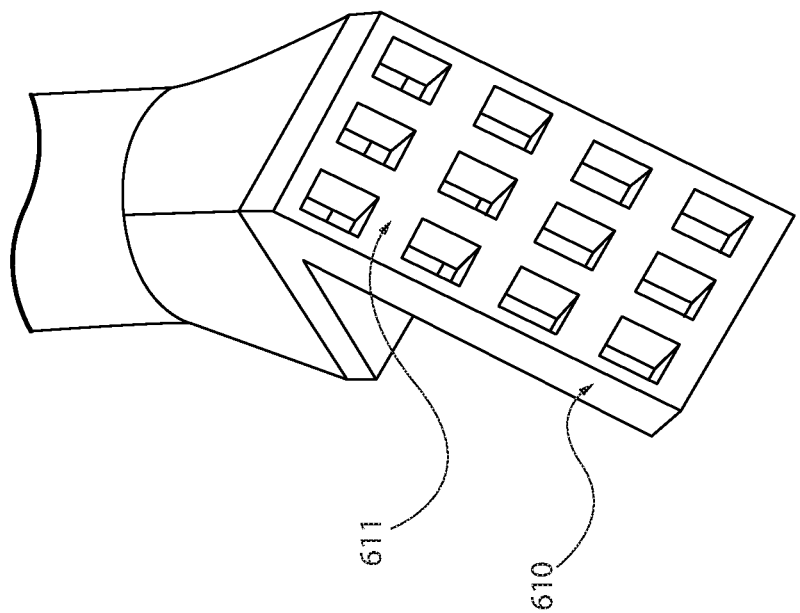
FIG. 6A-B illustrate embodiments of the present invention wherein the pick tool has a scooping or spatula portion.
Figure 6A:
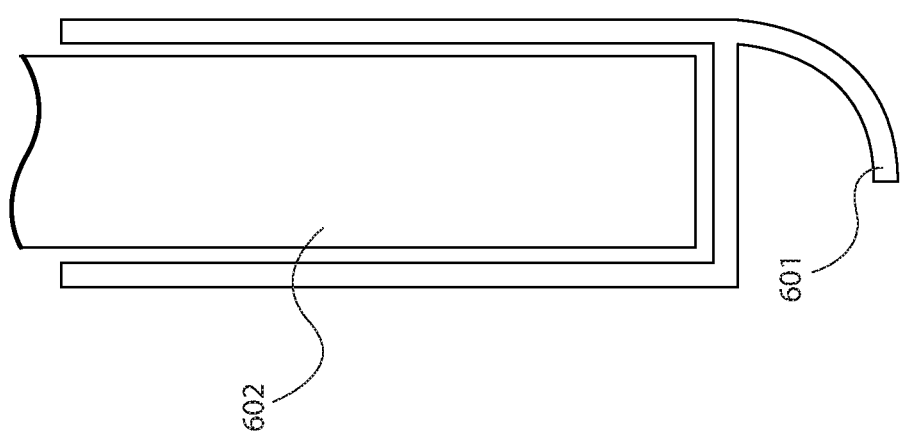

FIG. 6A illustrates another embodiment of a pick tool with a scooper tip 601. The tip 601 is affixed to the shaft 602 with a plastic sheath that fits over the end of the shaft 602. The scooper tip 601 may be removed between picks and/or disposable.

FIG. 6B illustrate another embodiment of a pick tool with a spatula 610 that will gather sample into aperture 611. The advantages of the grid configuration 610 for collecting sample are discussed in detail above.

Figure 7:
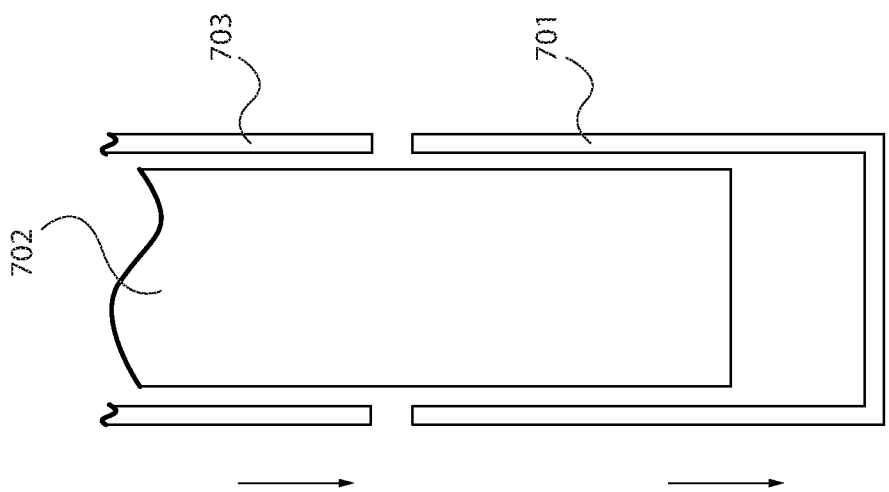
FIG. 7 illustrates another embodiment of a tip for the end portion of the pick tools illustrated in FIG. 1 that is a metal probe having a plastic sheath.

FIG. 7 illustrates an embodiment of the pick tool in which the sheath 701 is removeably engaged to the end of the shaft 702. The sheath 701, from which a scooping or other surface for collecting sample biomass extends, attaches to the shaft 702 with a gripping force (e.g., compression fit, magnetism). The shaft 702 is provided with a release mechanism 703 that will push the sheath 701 from the shaft 702 after use.

Figure 8:
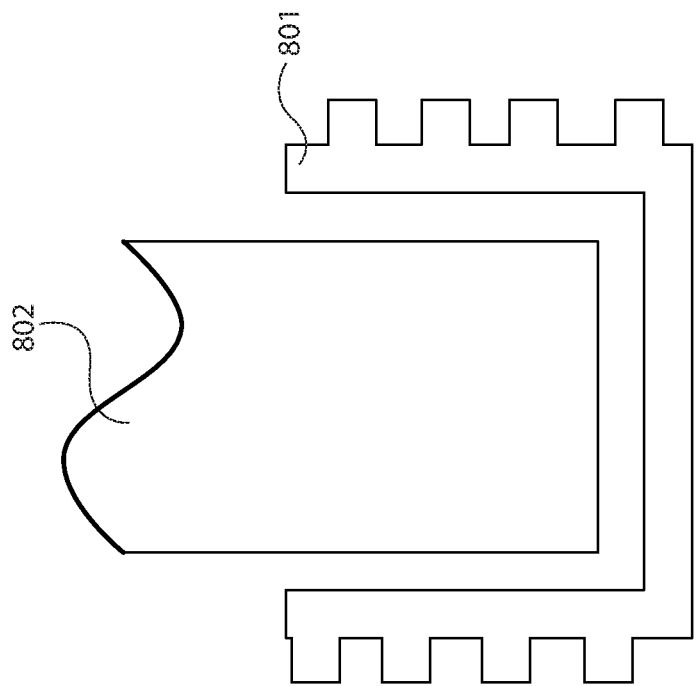
FIG. 8 illustrates another embodiment of a tip for the end portions of FIG. 1, which tip has a detachable sheath and a pushing mechanism for collecting microbes, in accordance with one embodiment of the present invention.

FIG. 8 is another embodiment where the sheath 801 screws on the end of the shaft 802. The sheath 601, 701, 801 can provide the pick tool with many functions. The sheath 601, 701, 801 allows for a smaller consumable in that the shaft 602, 702, 802 itself can be reused and only the sheath portion 601, 701, 801 is changed from use to use. The sheath 601, 701, 801 accommodates smart automated pick tool design as it accommodates the use of sensors and pressure transducers that allow for smart placement of the pick tool for both sample collection and depositing sample in solution.

The surface of the tip at the proximate end of the pick tool may be flocked, an open mesh, sintered beads, or other porous or rough surface. The tip may also be a molded design that facilitates sample biomass capture. The pick tool can be made of a variety of materials, including metal or polymer into which fine features may be molded or machined. However, the material should be biologically inert so as not to interfere with subsequent testing. The tip may be made of steel or aluminum or may also be molded from a polymeric material (e.g., polystyrene, polypropylene, polyethylene, polyvinyl chloride). Additionally, the pick tool may be made from a flexible or elastomeric material that allows the tool to pick up sample without damaging the media (e.g., agar) surface. The tip can be disposable or reusable depending on the material used. The tip may also be made from materials that are formulated or modified to have specific properties (e.g., hydrophilic properties or conductive properties) as noted above.

The pick tool may be used with a variety of methods for collecting a sample such as using a looping or rotating motion to contact and collect the sample. The pick tool may function as a pipette or vortex to draw the sample onto the tip. This may involve fluid flow or vacuum to facilitate pick of the organisms. Such is described above in the embodiments wherein the pick tool has a hollow core. In other embodiments, the pick tool collects the sample by simply touching the tip to the sample.

Additionally the tip of the pick tool as described herein may be made of a variety of materials and have a variety of surface treatments (e.g., surface roughening, chemical treatment or other modification). In this regard, the pick tool may be made of an off the shelf material or a specialized material that facilitates pick and release. The material can have additives or coatings or treatments applied to the surface to facilitate pick and release. Examples of said treatments include plasma or corona treatment either alone or followed by the addition of sodium dodecyl sulfate, triton, a self-assembling monolayer or other solution to alter the surface wettability or other properties of the tip.

FIG. 9 illustrates one embodiment of the pick tool and the one pick process for collecting and releasing sample. FIG. 9A has two components, a moldable pick rod 901 with fin 902 assembly and a sleeve 903 component. FIG. 9B shows the assembled components of FIG. 9A. In FIG. 9B, the moldable pick rod 901 and fin 902 assembly are inserted into the sleeve 903 in a raised position 905. Once in raised position 905, the pick tool is placed over a located colony 904. FIG. 9C shows the process of confining a particular colony and adjusting the sleeve 903 position prior to sample acquisition.

FIG. 9D illustrates the process of the colony pick. Whiles the pick tool is in a raised position 905 and in communication with the sample 904, the moldable pick rod 901 is pushed slightly downward in a rotating motion so that the fins 902 acquire sample 904 in the cavities 906 between the fin 902 and sleeve 903. Once the desired sample is acquired, the pick tool in the raised position 905 moves to the release process of FIG. 9E. The end of the pick tool with the sample 904 is encapsulated by collection tube 907. Next, the tube is mechanically pushed downward in a rotating motion that is opposite from that of the capture motion to a pushed out position 908. The downward rotating motion of the release exposes the fins 902 through the bottom of the sleeve 903 and the sample 904 contained in the cavities 906 is released into the collection tube 907 for further downstream processing.

There may be additional modifications to the pick tool to aid in release of the sample from the tool into solution for further processing. In some embodiments, magnetism or electrically conductive materials are used to further enhance organism acquisition. One embodiment illustrating a pick tool that uses magnetism for sample biomass acquisition is shown in FIG. 10. FIG. 10 is a magnetic stirrer 1003. The magnetic stirrer deploys scraper paddles 1008 that collect sample biomass from the surface on which the sample was cultured for testing (e.g., agar).

Figure 10C:
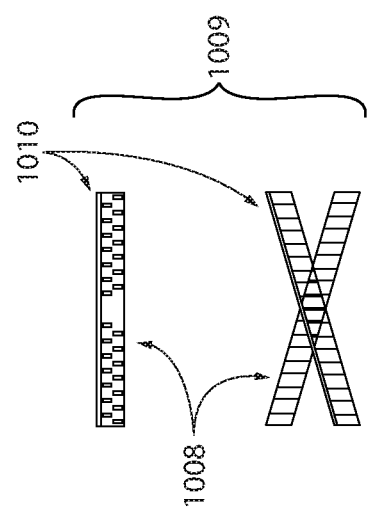
FIG. 10A-C illustrate unassembled portions of one embodiment of the invention that utilizes a magnetic stirrer assembly.
Figure 10B:
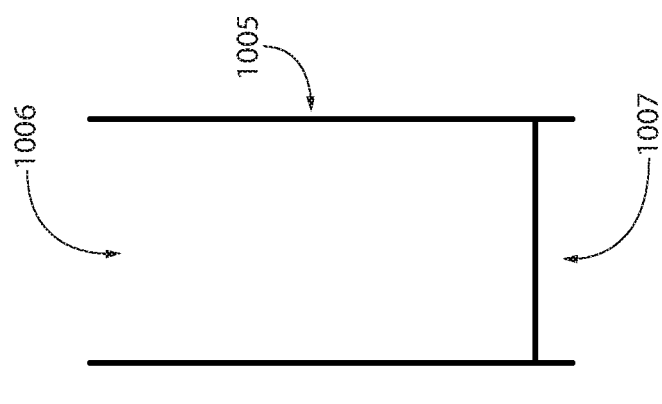
Figure 10A:
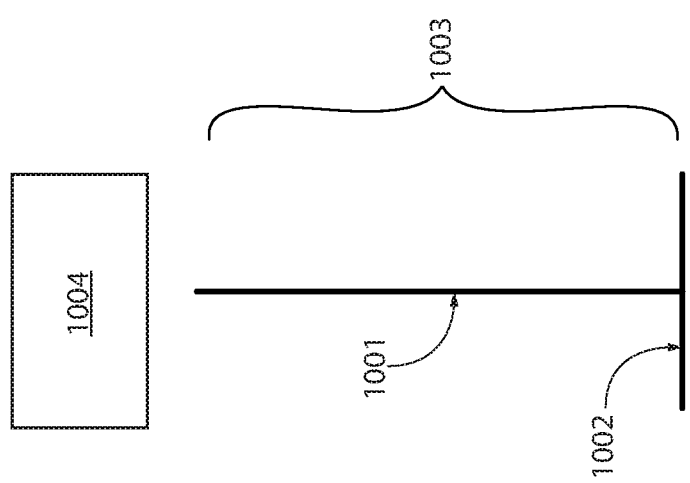

FIG. 10 illustrates unassembled portions of one embodiment of the invention that utilizes a magnetic stirrer assembly. FIG. 10A is a cut away side view of the assembly with a magnetic bar 1002 attached to a non-magnetic rod 1001. The magnetic stirrer assembly 1003 is controlled by a controller 1004. The controller 1004 activates the stirrer mechanism 1003. The activation causes the stirrer to rotate in a clockwise or counter clockwise direction. The controller is also configured to extend or retract the magnetic stirrer assembly 1003 in disposable tube 1005. (FIG. 11B) FIG. 10B illustrates a cut away side view of disposable tube 1005 with a top opening 1006 with an internal diameter that permits free rotation of the magnetic bar 1002 within the disposable tube 1005. The tube 1005 extends beyond the magnetic bar forming a recess 1007 in which the scraper 1008 fits. FIG. 10C shows a cut away side view and a perspective view of a disposable non-magnetic scraper 1008 that has a disposable ferromagnetic wire 1010 attached on the top thereof. The assembled disposable ferromagnetic scraper 1009 has a height approximately equal to the depression 1007 of the bottom of the tube 1005 in FIG. 10B.

FIG. 11 depicts the configuration of a magnetic pick tool prior to the picking process. FIG. 11A illustrates how magnetic stirrer 1003 is inserted into tube 1005 through the top opening 1006. Ferromagnetic scraper 1008 is placed at a standby location. FIG. 11B illustrates how the magnetic stirrer 1003 is advanced further down the tube 1005. The stirrer is advanced either manually or by automation. Automated mechanisms suited to advance the magnetic stirrer in the assembly are well known and not described in detail here. Ferromagnetic scraper 1008 is placed at a standby location. FIG. 11B illustrates how the tube 1005, along with the magnetic stirrer 1003, is positioned over the ferromagnetic scraper 1008 and attracts ferromagnetic scraper 1008 into the recess 1007 beneath the magnetic stirrer 1003 at the bottom of the tube 1005. Referring to FIG. 11C, colony 1101 is located on top of a biological inoculation surface 1102. FIG. 11D illustrates how the tube 1005 carrying the ferromagnetic scraper 1008, along with the magnetic stirrer 1003 is placed over the colony 1101.

Figure 12:
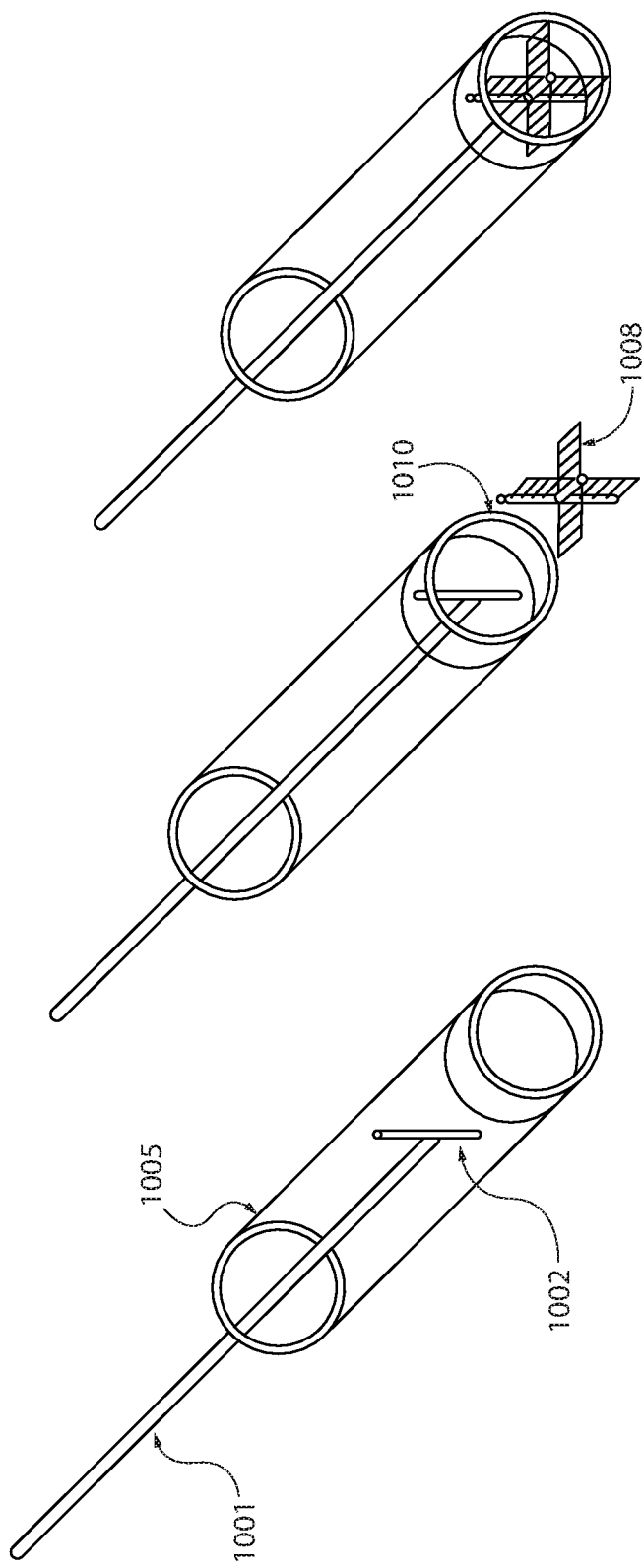
FIG. 12 shows a perspective view of the assemblies in FIGS. 11A, B, and C.

FIG. 12 depicts a perspective view of FIGS. 11A-C. FIG. 12 illustrates a wire 1010 affixed to the top of the non-magnetic scraper 1008. FIG. 12 also illustrates the assembly 1003 advanced down the tube 1005. FIG. 12 also illustrates the wire 1010 magnetically engaged with the magnetic bar 1002.

Figures 13A, 13B, 13C, 13D:
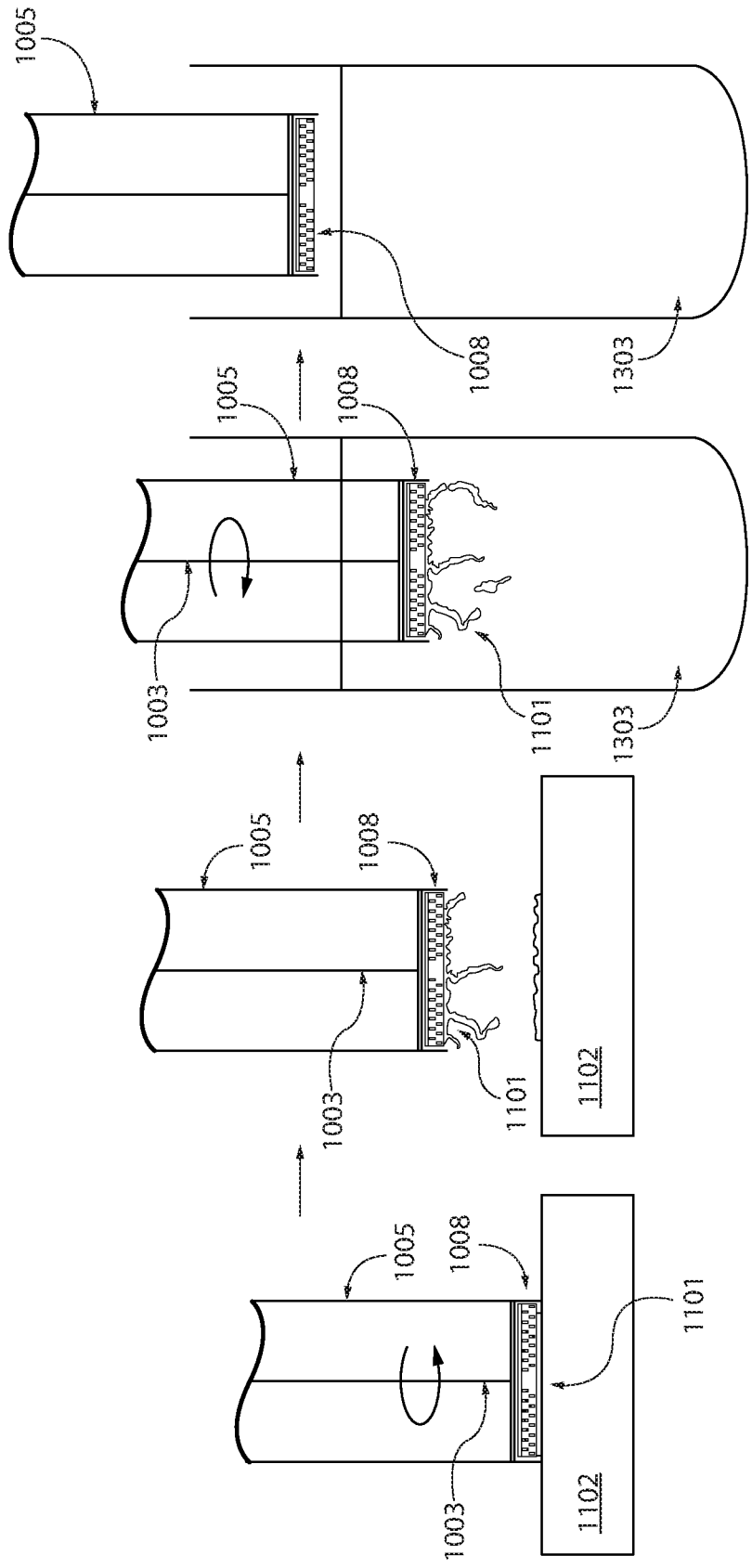
FIG. 13A-D illustrate the picking process using a magnetic stirrer assembly, in accordance with one embodiment of the invention using the tool illustrated in FIG. 11D.

FIG. 13 illustrates an embodiment of the magnetic one pick tool as it collects sample biomass from a sample and deposits the biomass in a liquid reagent vessel 1303. FIG. 13A illustrates the magnetic stirrer 1003 spinning in a counter clockwise direction to collect the sample. As such, the magnetic scraper 1008 has fins or paddles that are configured to collect sample onto the fins or paddles as the magnetic scraper is rotated. Again, the magnetic stirrer 1003 can be rotated manually or by automated mechanisms (e.g., robotic mechanism). Rotation of the stirrer assembly 1003 can be accomplished by electromechanical or electromagnetic mechanisms. Such mechanisms are well known in the art and not described in detail herein.

FIG. 13B illustrates the tube 1005 along with the magnetic stirrer 1003, the ferromagnetic scraper 1008, and collected sample biomass 1101 being withdrawn from the media surfaces 1102. FIG. 13C illustrates the tube 1005, along with the ferromagnetic scraper 1008 and collected colony 1101, being immersed into the liquid reagent vessel 1303. The magnetic stirrer 1003 spins (again by either manual or mechanical means), preferably in the opposite direction of FIG. 13A (e.g., clockwise), to release collected sample biomass 1101 into liquid reagent vessel 1303. Scraper 1008 is porous or mesh like which facilitates release of the sample into solution when the scraper 1008 is rotated in solution. FIG. 13D illustrates how the tube 1005, along with the ferromagnetic scraper 1008, is removed from the liquid reagent vessel 1303. The disposable scraper 1008 is released from the magnetic stirrer 1003. The scraper 1008 is discarded but the tube 1005 and stirrer assembly 1003 can be cleaned and reused. Alternatively, the ferromagnetic scraper 1008 can be released into liquid reagent vessel 1303 and used as a magnetic "stir bar" releasing sample as it spins in response to an externally applied magnetic field.

Figure 14:
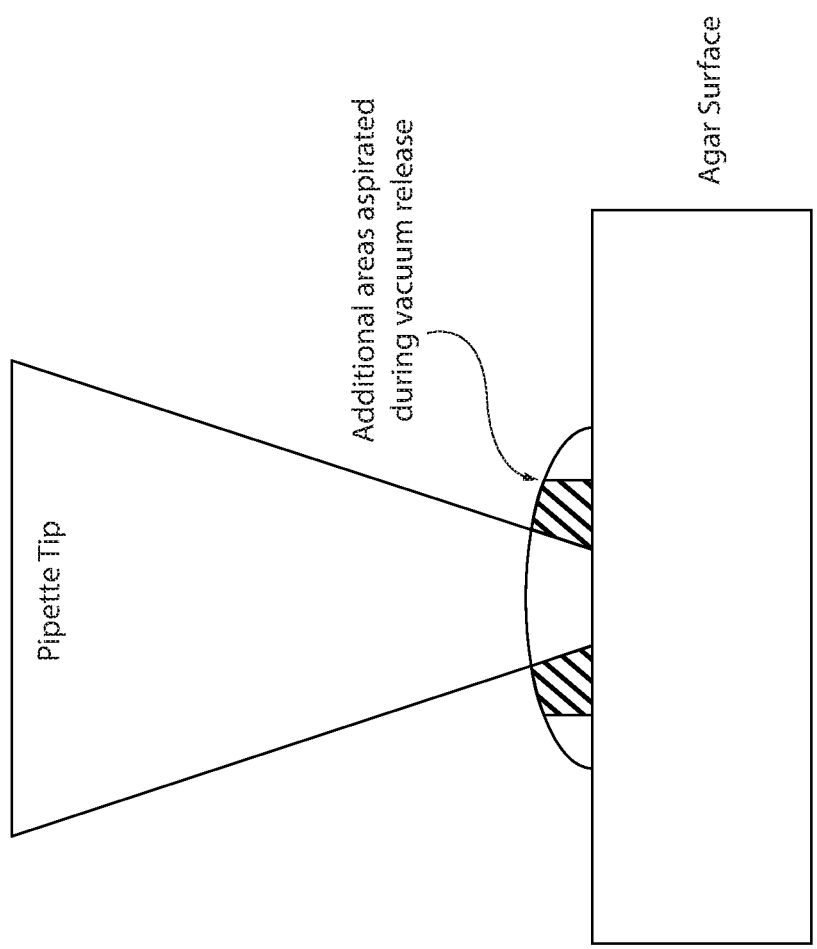
FIG. 14 illustrates a pipetting system as one embodiment of the invention.

In another embodiment, FIG. 14 depicts an automated pipetting system. In this embodiment, the pick tool is a pipette having a small inner diameter of about 0.2 mm to about 0.7 mm that is operable to facilitate picking of a sample from the media surface. In other embodiments the range of inner diameters is about 0.2 mm to about 0.5 mm. In some embodiments, the outer diameter can be up to about 1.2 mm or even larger. The outer diameter will depend upon the inner diameter and the thickness of the pipette material. The pipetting system is automated and designed using a capacitance detection system to allow the pipette to be lowered until the tip of the pipette is touching the agar surface containing the sample. The automated pipetting system can then lower the pipette further into the colony from about 0 to 1 mm. The lowering of the tip of the pipette allows the pipette to engage the agar surface without breaking the agar and forms a seal with the agar surface. Once the seal is formed, the pipette draws a volume of sample into the body of the pipette. This creates a vacuum within the pipette tip and allows a higher volume of sample to be collected. The volume of sample collected can be about 1 mL or more.

Once the volume of sample is collected, the pipette is slowly retracted from the agar surface. The slow retraction of the pipette creates suction in and around the tip that effectively vacuums the organism off the agar surface. More sample may be vacuumed off the agar surface to create higher densities of microorganisms (i.e., greater numbers of CFUSs per volume). As shown in FIG. 14, microorganisms near the outside of the tip are drawn into the pipette in addition to the portion of the colony initially captured within the tip by virtue of the decent of the tip into the colony of interest.

After the sample has been acquired, in yet another embodiment, the pipetting system can perform a series of rapid draws and dispenses of the pipette tip in the liquid suspension. For example, the pipetting system can repeat the series of withdraws up to about 24 times within a 20 second period and dispense about 250 μL of a 300 μL sample. The repetitive action creates high shear forces at the tip of the pipette. The high shear forces allow the dispersion of clumps or mucoid stands of the sample containing microorganisms to create a more uniform suspension.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An automated method for collecting a biological sample from a semi-solid surface comprising:
   providing a robotic pipettor adapted to receive a pipette tip,
   lowering the pipette tip until it contacts the semi-solid surface on which a colony of interest is disposed such that the pipette tip is in contact with the colony of interest, advancing the pipette tip further until the pipette tip is in contact with the semi-solid surface supporting the colony of interest thereby forming a seal with the semi-solid surface;
   collecting, using air assist, a portion of the biological sample;
   retracting the pipette tip from contact with the semi-solid surface and the colony of interest;
   placing the pipette tip in contact with a fluid disposed in a vessel;
   dispensing, using air assist, a portion of the contents from the pipette tip into solution and then drawing at least a portion of the biological sample back into the pipette tip thereby introducing shear force onto a portion of the biological sample collected by the pipette tip; and
   dispensing, using air assist, at least a portion of the biological sample from the pipette tip into the solution.

2. The method of claim 1 wherein the semi-solid surface is a surface of nutrient media.

3. The method of claim 1 further comprising monitoring the capacitance of the pipette tip wherein a change in monitored capacitance is indicative of contact between the pipette tip and the colony of interest.

4. The method of claim 3 comprising continuing to monitor the capacitance of the pipette tip until a change in capacitance indicates contact between the pipette tip and the biological sample.

5. The method of claim 1 wherein the pipette tip has an opening through which the portion of the biological sample is collected and that opening has an inner diameter of about 0.2 mm to about 0.7 mm.

6. The method of claim 5 wherein the inner diameter is about 0.2 mm to about 0.5 mm and the outer diameter is up to about 1.2 mm.

* * * * *